United States Patent [19]
Kuepper et al.

[11] Patent Number: 5,496,298
[45] Date of Patent: Mar. 5, 1996

[54] ELASTOMERIC EARS FOR DISPOSABLE ABSORBENT ARTICLE

[75] Inventors: Rebecca J. Kuepper, Appleton; Christine A. Rasmussen, Medford, both of Wis.

[73] Assignee: Kimberly-Clark Corporation, Neenah, Wis.

[21] Appl. No.: 174,565

[22] Filed: Dec. 28, 1993

[51] Int. Cl.⁶ .................................................. A61F 13/15
[52] U.S. Cl. ...................... 604/389; 604/385.2; 604/358; 428/284
[58] Field of Search ............................. 604/385.1, 385.2, 604/358, 389; 428/284, 913

[56] References Cited

U.S. PATENT DOCUMENTS

| | | | |
|---|---|---|---|
| 3,902,236 | 9/1975 | Deem | 29/256 |
| 4,050,462 | 9/1977 | Woon et al. | 128/287 |
| 4,076,663 | 2/1978 | Masuda et al. | 260/17.4 GC |
| 4,205,679 | 6/1980 | Repke et al. | 128/287 |
| 4,286,082 | 8/1981 | Tsubakimoto et al. | 526/240 |
| 4,300,562 | 11/1981 | Pieniak | 128/287 |
| 4,323,070 | 4/1982 | Ternstrom et al. | 128/287 |
| 4,381,781 | 5/1983 | Sciaraffa et al. | 604/372 |
| 4,527,990 | 7/1985 | Sigl | 604/385 A |
| 4,573,991 | 3/1986 | Pieniak et al. | 604/385 A |
| 4,663,220 | 5/1987 | Wisneski et al. | 428/221 |
| 4,704,116 | 11/1987 | Enloe | 604/385 A |
| 4,731,066 | 3/1988 | Korpman | 604/366 |
| 4,798,603 | 1/1989 | Meyer et al. | 604/378 |
| 4,834,738 | 5/1989 | Kielpikowski et al. | 604/385.2 |
| 4,838,885 | 6/1989 | Bernardin | 604/385.1 |
| 4,846,825 | 6/1989 | Enloe et al. | 604/385.1 |
| 4,850,990 | 7/1989 | Huntoon et al. | 604/385.2 |
| 4,872,871 | 10/1989 | Proxmire et al. | 604/394 |
| 5,147,347 | 9/1992 | Huang | 604/390 |
| 5,149,335 | 9/1992 | Kellenberger et al. | 604/372 |
| 5,226,992 | 7/1993 | Morman | 156/62.4 |

FOREIGN PATENT DOCUMENTS

| | | |
|---|---|---|
| 0215408B1 | 3/1987 | European Pat. Off. . |
| 0217032A2 | 4/1987 | European Pat. Off. . |
| 0320991A2 | 6/1989 | European Pat. Off. . |
| 0323634A2 | 7/1989 | European Pat. Off. . |
| 0338680A2 | 10/1989 | European Pat. Off. . |
| 0388681A2 | 9/1990 | European Pat. Off. . |
| 0421473A3 | 4/1991 | European Pat. Off. . |
| 0433951A3 | 6/1991 | European Pat. Off. . |
| 0528282A3 | 2/1993 | European Pat. Off. . |
| 0532034A3 | 3/1993 | European Pat. Off. . |
| 0570980A1 | 11/1993 | European Pat. Off. . |
| 2552662A1 | 4/1985 | France . |
| 2214057A | 8/1989 | United Kingdom . |
| 2236663 | 4/1991 | United Kingdom . |
| 2267024 | 11/1993 | United Kingdom . |

OTHER PUBLICATIONS

U.S. Ser. No. 07/757,760 entitled "Thin Absorbent Article Having Rapid Uptake of Liquid" filed Sep. 11, 1991 (abandoned) in the name of William D. Hanson et al.
U.S. Ser. No. 08/096,654 entitled, "Thin Abosrbent Article Having Rapid Uptake of Liquid" filed Jul. 22, 1993 in the name of William D. Hanson et al.
U.S. Ser. No. 08/148,130 entitled "Mechanical Fastening Tapes And Method For Their Construction" filed Nov. 5, 1993 in the name of Rebecca L. Dilnik et al.

*Primary Examiner*—James J. Bell
*Attorney, Agent, or Firm*—Thomas J. Mielke

[57] ABSTRACT

Disclosed is an elastomeric ear suitable for use on a disposable absorbent article. The elastomeric ear is formed from an elastomeric material which defines a proximal edge, a distal edge, a first connecting edge and a second connecting edge. The first and second connecting edges connect the proximal and distal edges. The second connecting edge is non-parallel to the first connecting edge, and the proximal edge is longer than the distal edge. A fastener is joined to the elastomeric ear. Also described is a disposable absorbent article including such an elastomeric ear.

30 Claims, 4 Drawing Sheets

ELASTOMERIC EARS FOR DISPOSABLE ABSORBENT ARTICLE

BACKGROUND OF THE INVENTION

The present invention relates to disposable article. Specifically, the present invention relates to elastomeric ears suitable for use on disposable absorbent articles.

Disposable absorbent articles such as disposable diapers, training pants, adult incontinence garments, and the like are known. In the past, particularly in the case of infant diapers, such absorbent articles were generally formed with an hourglass configuration. The narrower portion of the article was adapted to be placed between the legs of the wearer with the wider portions of the article being adapted to encircle the waist of a wearer so that the front and rear portions overlapped and could be easily attached to one another. Recently, it has become desirable to produce absorbent articles, such as infant diapers, which fit more closely to the body of a wearer. Accordingly, it has become desirable to make such articles smaller and less conspicuous in use while still maintaining a high level of absorbent protection. Specifically, it has become desirable to produce disposable absorbent articles which have a relatively narrow crotch section and a narrower overall width when compared to typical disposable absorbent articles.

Leg openings are defined, in part, on traditional infant diapers by the overlapped front and rear portions of the diaper. Such leg openings are generally perceived as providing good absorbent protection. If the front and rear portions of the diaper do not completely encircle the waist of a wearer and overlap with one another, there is a perception of decreased leakage performance.

Known fastening devices for absorbent articles which do not completely encircle the waist of a wearer have generally consisted of relatively narrow rectangular means or beltlike means to hold the article in place around the waist of a wearer. Such known means do not generally correct for the perceived decrease in absorbent performance. Further, known means of fastening such articles about the waist of a wearer can lead to undesirable red marking of the skin of a wearer.

Accordingly, it is desirable to provide an improved disposable absorbent article which corrects for the perceived deficiencies and undesirable aspects of known disposable articles.

SUMMARY OF THE INVENTION

In one aspect, the present invention relates to a disposable absorbent article. The article defines a front portion, a rear portion, and a crotch portion connecting the front and rear portions. The article comprises an outer cover, a liquid-pervious bodyside liner, an absorbent material located between the cover and the bodyside liner, a pair of elastomeric ears attached to a rear portion of the article, and a fastener attached to the ears for attaching the elastomeric ears to a front portion of the article. The elastomeric ears have a proximal edge, a distal edge, a first connecting edge, and a second connecting edge. The first and second connecting edges connect the proximal and distal edges. The second connecting edge is non-parallel to the first connecting edge, and the proximal edge is longer than the distal edge.

In another aspect, the present invention is directed to a elastomeric ear adapted for use on a disposable absorbent article. The ear comprises a body of elastomeric material. The elastomeric material defines a proximal edge, a distal edge, a first connecting edge, and a second connecting edge. The first and second connecting edges connect the proximal and distal edges. The second connecting edge is non-parallel to the first connecting edge, and the proximal edge is longer than the distal edge. The elastomeric ear further comprises a fastener joined to the elastomeric ear for releasably attaching the elastomeric ear to a substrate.

DETAILED DESCRIPTION OF THE PREFERRED EMBODIMENT

The present invention relates to disposable absorbent articles. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. While the present description will be made in the context of a diaper article, it should be understood that the present invention is also applicable to other disposable personal care absorbent articles, such as adult incontinence garments, children's training pants, and the like.

Figure 1:
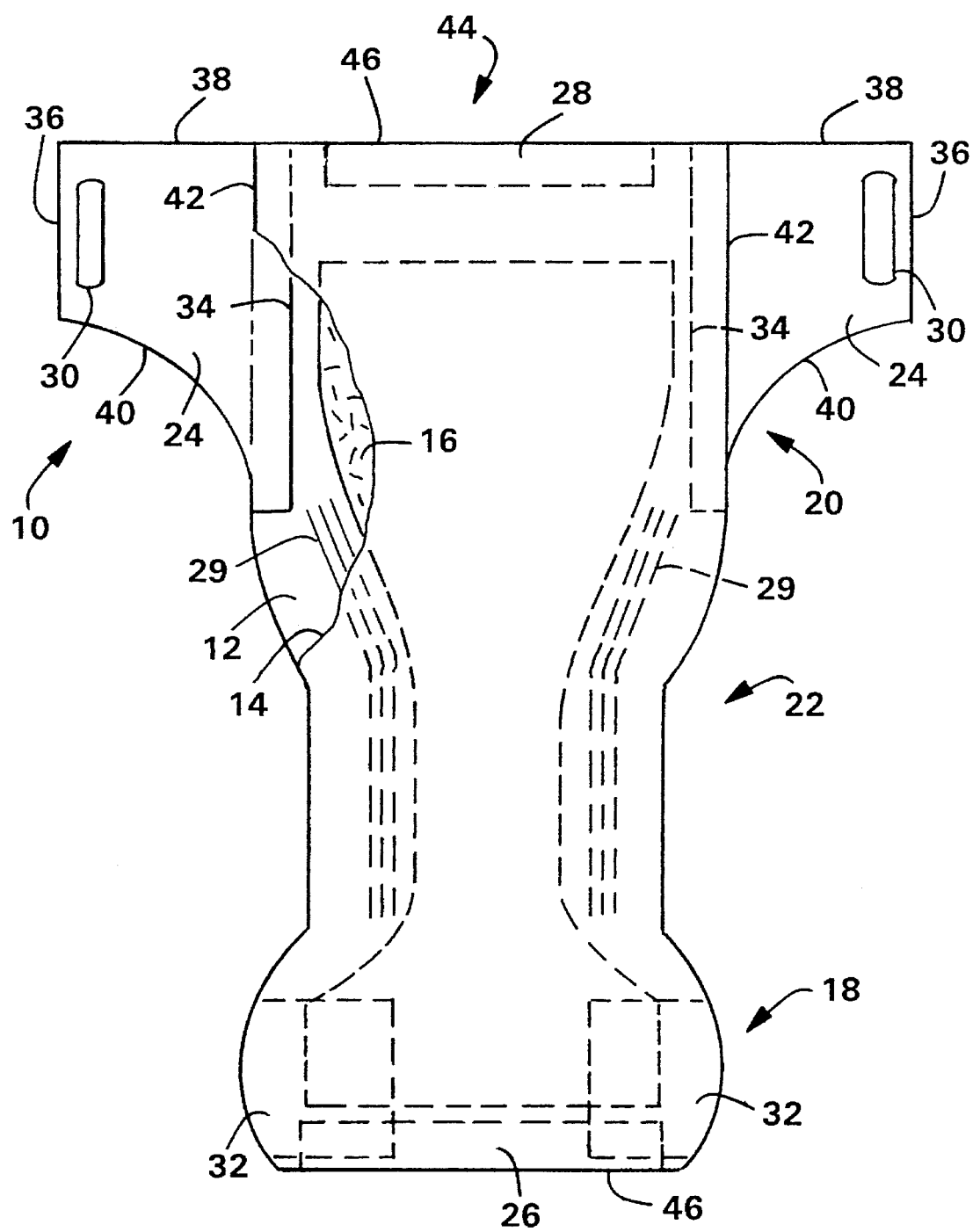
FIG. 1 illustrates a disposable absorbent article according to the present invention.

Referring to the figures wherein like numbers represent like elements, FIG. 1 illustrates an absorbent article such as a diaper 10, including an outer cover 12 and a liquid-pervious bodyside liner 14, which is disposed in facing relation with the outer cover 12. An absorbent material 16 is disposed between the outer cover 12 and the bodyside liner 14. The diaper 10 defines a front portion 18, a rear portion 20, and a crotch portion 22 connecting the front and rear portions. A pair of elastomeric ears 24 are joined to the rear portion 20 of the diaper 10. The elastomeric ears are adapted, in use, to overlap with the front portion 18 of the diaper 10. The diaper further comprises front waist elastic member 26 attached to the front portion 18, rear waist elastic member 28 attached to the rear portion 20 and leg elastics 29 attached to the crotch portion 22. The elastomeric ears 24 comprise fasteners 30 joined to the elastomeric ears 24 for releasably attaching the elastomeric ears to a substrate such as the front portion 18 of diaper 10. In the embodiment illustrated in FIG. 1, fastener 30 comprises a mechanical fastener such as the hook portion of a hook-and-loop material. Accordingly, in the illustrated embodiment, the diaper 10 further comprises loop material 32 attached to the front portion 18 of diaper 10.

The elastomeric ears 24 include a proximal edge 34, an opposed distal edge 36, a first connecting edge 38, and a second connecting edge 40. As used herein, the proximal edge is that edge of the elastomeric ears 24 which is joined to lateral edges 42 of diaper body 44 defined by, in the illustrated embodiment, outer cover 12 and bodyside liner 14. The distal edge 36 is that edge of elastomeric ear 24 which is opposite the proximal edge 34 moving in a direction outward from a central longitudinal axis of the diaper 10. The first and second connecting edges 38 and 40 connect the proximal edge 42 and the distal edge 36 thereby defining a body of elastomeric material which at least partially defines elastomeric ear 24.

As used herein, reference to two materials or elements being "joined" refers to the situation wherein the two materials or elements are directly joined to one another or where they are indirectly joined to one another such as where both are joined to an intermediate element. Similarly, methods of joining two materials or elements include forming the elements or materials integrally, or attaching the elements together such as through the use of adhesive, sonic or thermal bonding, sewing, and the like.

As can be seen from reference to FIG. 1, elastomeric ear 24 is, in the illustrated embodiment, joined to diaper body 44 by adhesively sandwiching proximal edge 34 between the outer cover 12 and bodyside liner 14.

As will be explained in greater detail below, the diaper 10, including diaper body 44 and elastomeric ears 24, may be configured such that, in use, transverse ends 46 of diaper body 44 do not extend completely around the waist of a wearer. That is, diaper body 44 is dimensioned such that, in use, portions of diaper body 44 do not overlap around the waist of a wearer. Instead, joining of the front and rear portions about the waist of a wearer occurs as a result of the elastomeric ears 24. Thus, in use, the elastomeric ears 24 may contact the skin of a wearer directly, and first connecting edge 38 may form part of the waist opening, and second connecting edge 40 may form part of a leg opening of the diaper 10 when in use on a wearer.

When the elastomeric ear 24 is to form a joining function between the front and rear portions such that the second connecting edge 40 of the elastomeric ear 24 forms part of a leg opening of a diaper, Applicants have found certain design features of the elastomeric ear 24 to be important. Certain of the important design features of the elastomeric ears according to the present invention can be seen by reference to FIGS. 2–4.

Figure 2:
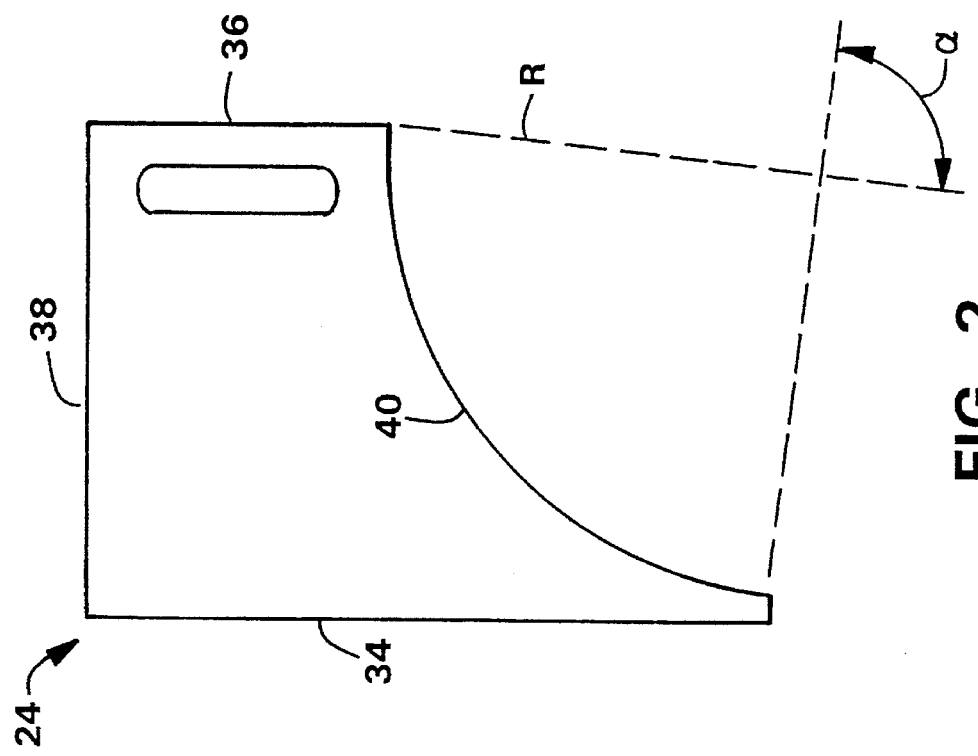
FIG. 2 illustrates one embodiment of an elastomeric ear according to the present invention.

With reference to FIG. 2, elastomeric ear 24 is illustrated as defining proximal edge 34, distal edge 36, first connecting edge 38, and second connecting edge 40. In the embodiment illustrated in FIG. 2, proximal edge 34 and distal edge 36 are generally parallel, and both are linear. As proximal edge 34 is to be joined to an absorbent article, it is generally preferred that proximal edge 34 be generally linear. Distal edge 36 can take any of a number of configurations. For example, it may be linear, arcuate, undulating, notched, or the like.

In FIG. 2, the first connecting edge 38 is generally perpendicular to proximal edge 34. While this is believed to be a preferred relationship, it is also believed that first connecting edge 38 can be in a non-perpendicular relationship with the proximal edge 34.

The first connecting edge 38 and second connecting edge 40 are non-parallel. Applicants have discovered that it is desirable to have the second connecting edge 40 be concavely arcuate. More specifically, Applicants have discovered that it is preferable to have the second connecting edge be defined by an arc of a circle having a radius of from about 1 inch (2.54 centimeters) to about 6 inches (15.24 centimeters), desirably of from about 1.5 inches (3.8 centimeters) to about 4 inches (10.2 centimeters), and preferably of from about 2 inches (5.1 centimeters), to about 3.5 inches (8.9 centimeters). With reference to FIG. 2, the letter "R" designates the radius of the circle which defines the second connecting edge 40. As can also be seen from FIG. 2, the arc which defines the second connecting edge 40 defines an included angle alpha. When the second connecting edge 40 is defined by an arcuate segment of a single circle, it is preferred that the included angle alpha be from about 50 to about 130 degrees, preferably of from about 80 to about 100 degrees.

Figure 3:
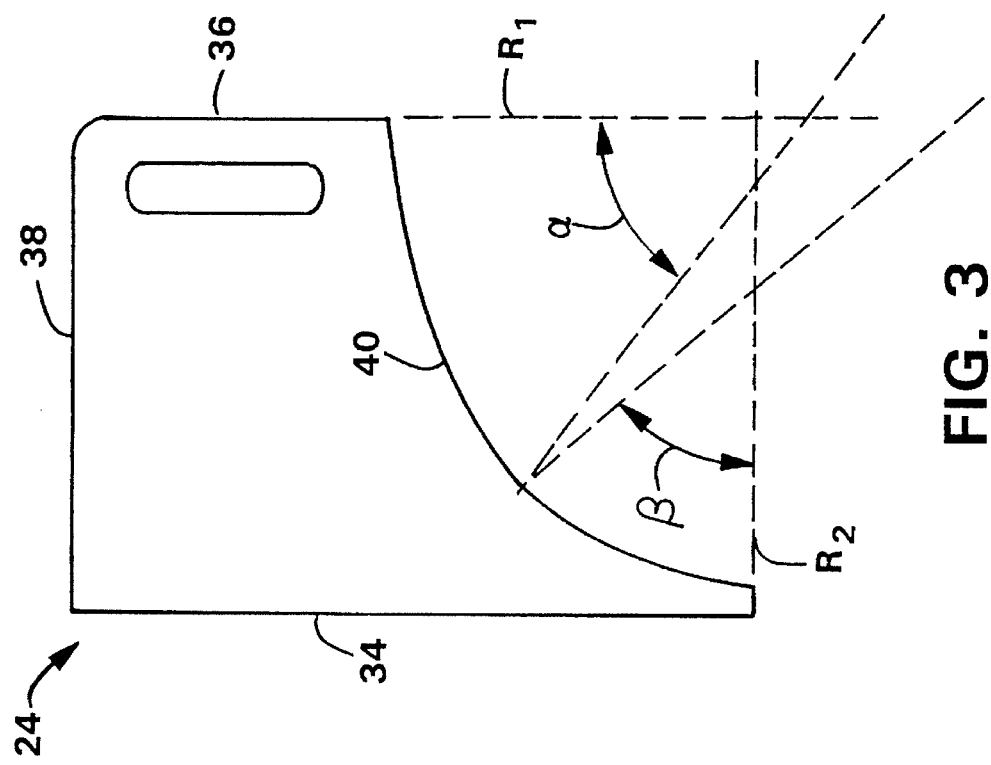
FIG. 3 illustrates an elastomeric ear according to a second embodiment of the present invention.

An alternate embodiment of an ear according to the present invention is illustrated in FIG. 3. In FIG. 3, the second connecting edge 40 is defined by an arc along the circumference of two circles. Again, the first circle has a radius of $R_1$ and defines included angle alpha, while the second circle has a radius of $R_2$ and defines included angle beta. Together arcuate segments along the circumference of the two circles defined by $R_1$ and $R_2$ define the second connecting edge 40. Again, $R_1$ and $R_2$ should be within the ranges set forth above in connection with FIG. 2. Furthermore, the sum of included angle alpha and included angle beta should be within the range described above in connection with angle alpha illustrated in FIG. 2.

While FIGS. 2 and 3 illustrate the situation wherein the second connecting edge 40 is defined by one and two circles, respectively, it is to be understood that the second connecting edge 40 could be defined by three, four, or more circles.

As a general rule, the proximal edge 34 will have a length of from about 2 inches (5.1 centimeters) to about 7 inches (17.8 centimeters), preferably of from about 3 inches (7.6 centimeters) to about 6 inches (15.2 centimeters), and most preferably of from about 3.5 inches (8.9 centimeters) to about 5.5 inches (14.0 centimeters). Similarly, the distal edge 36 will have a length equal to from about 0.25 to about 1.0 times the length of the radius of the circle defining the second connecting edge 40.

Accordingly, the distal edge 38 generally has a length of from about 0.25 inch (0.635 centimeter) to about 6 inches (15.24 centimeters), preferably of from about 1 inch (2.54 centimeters) to about 3 inches (7.6 centimeters).

Further, the ratio of the length of the distal edge to the proximal edge is suitably from about 1:28 to about 3:4, beneficially of from about 1:4 to about 1:2

Applicants have discovered that, by configuring the elastomeric ear 24 as described above, certain advantages are achieved. Specifically, when an elastomeric ear 24 is used as described herein, Applicants have discovered that improved diaper fit is achieved. Specifically, the elastomeric ears provide for leg and hip coverage, which coverage has, in the past, been provided by the overlapping sections of the front and rear portions of conventional infant diapers. Moreover, the elastomeric ears have been found to reduce the incidence of red marking on the skin of a wearer when compared to elastomeric ears not having the described configurations. Both of these features lead caretakers to understand that the elastomeric ears of the present invention are providing a better fit and more comfort for the wearer.

If the radius of the circle is below about 1 inch (2.54 centimeters), too much of the wearer's leg or hip will be exposed. If the radius of the circle is greater than about 6 inches (15.24 centimeters), there is not enough curve defined in the second connecting edge 40, and red marking of a wearer's skin can result.

Figure 4:
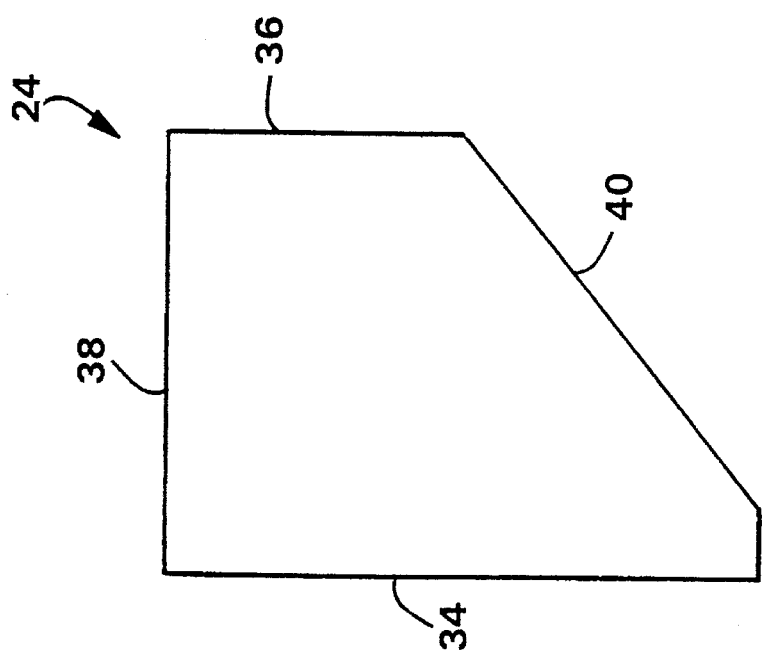
FIG. 4 illustrates an elastomeric ear according to a third embodiment of the present invention.

While it is generally preferred that the second connecting edge 40 has a concavely arcuate configuration, FIG. 4 illustrates the situation wherein the second connecting edge 40 is generally linear. While the configuration illustrated in FIG. 4 may be acceptable in some situations, it is generally not preferred.

Figure 5:
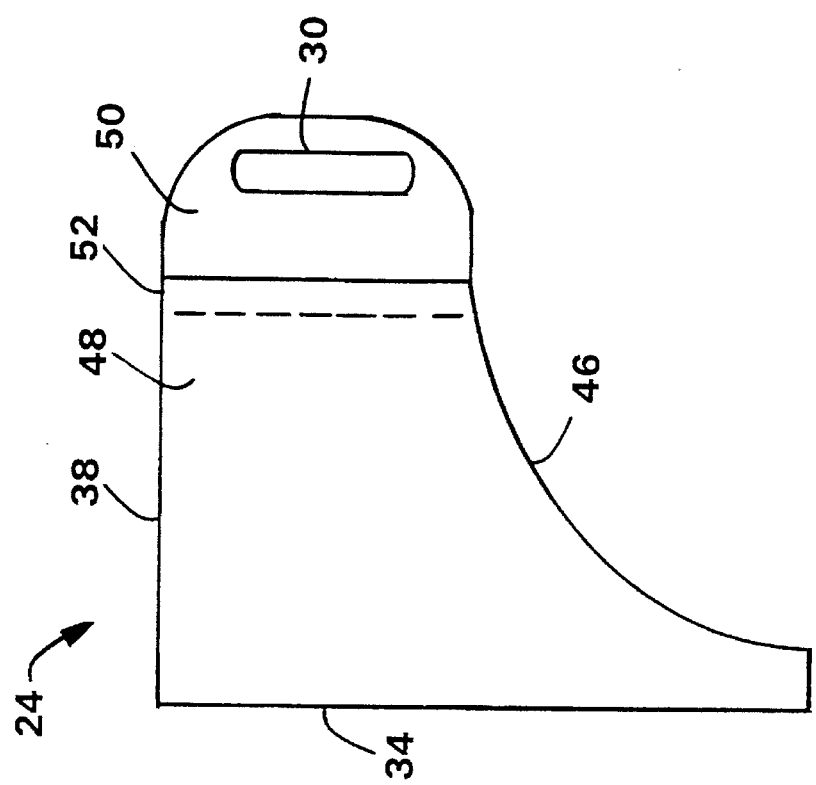
FIG. 5 illustrates an elastomeric ear according to a fourth embodiment of the present invention.

FIG. 5 illustrates a third alternative embodiment of an elastomeric ear according to the present invention. In the embodiment illustrated in FIG. 5, the main body 48 of elastomeric ear 24 is elastomeric and has the configuration described above. An extension member 50 is attached to the main body 48 along seam 52. The extension member 50 may be elastomeric or non-elastomeric. In one preferred embodiment, the extension member 50 is non-elastomeric. Fastener 30 (such as a hook material) is illustrated as being attached to the extension 50. When the fastener 30 is attached to the extension member 50 and the extension member 50 is non-elastomeric, the fastener 30 tends to remain flat. In contrast, when the fastener 30 is attached to an elastomeric substrate, the edges of the fastener 30 may curl outward so that it is more difficult to engage the fastener 30 with loop material 32. The extension member 50 may take any of a number of different configurations. The seam 52 may be formed by adhesive bonding, sonic or thermal bonding, or any other suitable means.

Figure 6:
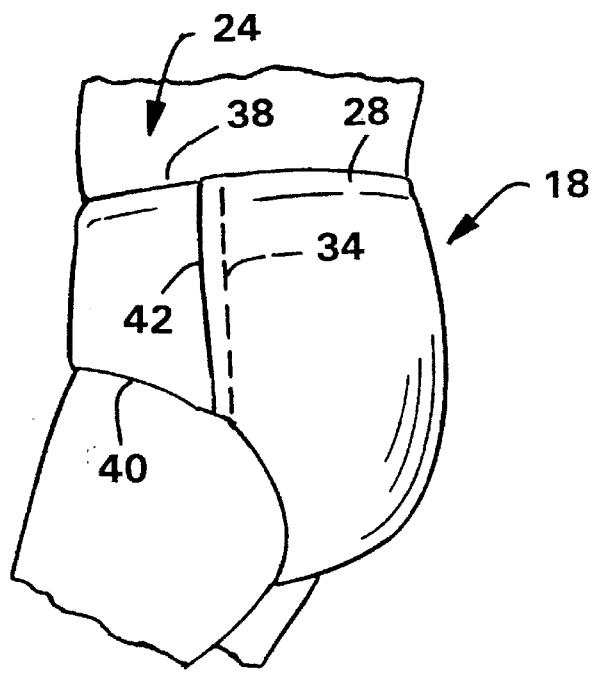
FIG. 6 illustrates a side view of the disposable absorbent article illustrated in FIG. 1 in use on a wearer.
Figure 7:
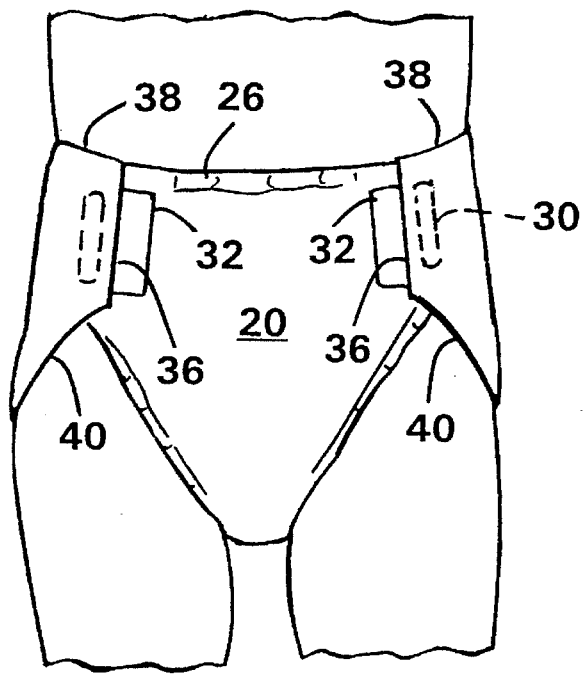
FIG. 7 illustrates a frontal view of the disposable absorbent product illustrated in FIG. 1 in use on a wearer.

FIGS. 6 and 7 illustrate the infant diaper illustrated in FIG. 1 in use on a wearer. As can be seen from reference to FIGS. 6 and 7, the elastomeric ears 24 serve to connect rear portion 18 and front portion 20 along the sides of a wearer. The first connecting edges 38 define a portion of a waist-encircling edge while the second connecting edges 40 serve to define a portion of a leg opening. The concavely arcuate nature of the second connecting edge 40 defines a smooth, aesthetically pleasing line of junction across the leg of a wearer. The fastener 30 attaches to the loop material 32 to provide a closure function.

The bodyside liner 14 presents a body-facing surface which is compliant, soft feeling, and non-irritating to the wearer's skin. Further, bodyside liner 14 may be less hydrophilic than the absorbent material 16 and is sufficiently porous to be liquid pervious, permitting a liquid to readily penetrate through its thickness. A suitable bodyside liner 14 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 14 is typically employed to help isolate the wearer's skin from liquids held in the absorbent material 16.

Various woven and nonwoven fabrics can be used for bodyside liner 14. For example, the liner may be composed of a meltblown or spunbonded web of polyolefin fibers. The bodyside liner may also be a bonded-carded web composed of natural and synthetic fibers. For the purposes of the present description, the term "nonwoven web" shall mean a web of material which is formed without the aid of a textile weaving or knitting process.

The bodyside liner may be composed of a substantially hydrophobic material, and the hydrophobic material may optionally be treated with a surfactant or otherwise processed to impart a desired level of wettability and hydrophilicity. In a particular embodiment of the present invention, bodyside liner 14 is a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent Triton X-102 surfactant.

The outer cover 12 may be composed of a liquid-permeable material but preferably comprises a material which is configured to be substantially impermeable to liquids. For example, a typical outer cover can be manufactured from a thin plastic film or other flexible liquid-impermeable material. Outer cover 12 generally prevents the exudates contained in the absorbent material 16 from wetting articles, such as bed sheets and overgarments, which contact the diaper 10. In a particular embodiment of the present invention, the outer cover 12 is a polyethylene film having a thickness of from about 0.012 millimeter (0.5 mil) to about 0.051 millimeter (2.0 mils). In a preferred embodiment, the outer cover is a film having a thickness of about 1.25 mil. In an alternative preferred embodiment of the present invention, the outer cover 12 is a stretch thermal laminate comprising a 0.6 mil (0.015 millimeter) polypropylene blown film and a 0.7 ounce per square yard (23.6 grams per square meter) polypropylene spunbond material. The spunbond material is composed of about 2.0 denier fibers. The stretch thermal laminate is formed by stretching the polypropylene film, in one direction, until it is extended by 25 percent. The spunbond polypropylene is then brought into face-to-face contact with the stretched polypropylene film. The polypropylene film and spunbond material are then thermally bonded together at spaced intervals. The resulting laminate has a plurality of separate and distinct bond sites with an overall bond area of about 13 percent per unit area. After the film and spunbond material are laminated to one another, the laminate is allotted to relax. The film layer retracts about 10 percent, thereby leaving the film permanently deformed to a length of about 15 percent greater than its original length. The process for forming the stretch thermal laminate is described in greater detail in commonly-owned copending U.S. patent application Ser. No. 07/997,800, filed Dec. 29, 1992, in the name of McCormack et al., the contents of which are incorporated herein.

The size of the outer cover 12 is typically determined by the size of the absorbent material 16 and the exact diaper design selected. Outer cover 12, for example, may be generally T-shaped, generally I-shaped, or may have a modified hourglass shape, and may extend beyond the terminal edges of the absorbent material 16 by a selected distance, such as a distance within the range of from about 1.3 centimeters to about 2.5 centimeters (about 0.5 to about 1.0 inch).

The bodyside liner 14 and outer cover 12 are joined together in an operable manner. As stated above, the term "joined" encompasses configurations in which the bodyside liner 14 is directly joined to the outer cover 12 by affixing liner 14 directly to outer cover 12, and configurations wherein liner 14 is joined to outer cover 12 by affixing liner 14 to intermediate members which, in turn, are affixed to outer cover 12. The liner 14 and outer cover 12 can be affixed directly to each other in the diaper periphery by attachment means (not shown) such as adhesive bonds, sonic bonds, thermal bonds, or any other attachment means known in the art. For example, a uniform continuous layer of adhesive, a patterned layer of adhesive, a sprayed pattern of adhesive, or an array of separate lines, swirls, or spots of construction adhesive may be used to affix the bodyside liner 14 to outer cover 12. The above-described attachment means may also be employed to interconnect and assemble together the other component parts of the absorbent article.

Front waist elastic member 26 and rear waist elastic member 28 are suitably formed from any elastic material capable of extending at least about 10 percent, preferably at least about 50 percent. The waist elastic members may be composed of any suitable elastomeric material, such as an elastomer film, an elastic foam, multiple elastic strands, an elastomeric fabric, or the like. For example, suitable elastic waist constructions are described in U.S. Pat. No. 4,916,005 to Lippert et al., the disclosure of which is hereby incorporated by reference to the extent that it is consistent (not contradictory) herewith. The front and rear waist elastic members are secured to the diaper 10 in an elastically contractible condition so that, in a normal, unrestrained configuration, the elastic members effectively contract against diaper 10. The front and rear waist elastic members may be attached in at least two ways. For example, the elastic members may be stretched and secured to diaper 10 while diaper 10 is in an uncontracted condition. Alternatively, diaper 10 may be contracted, for example, by pleating, and the elastic member secured and connected to the diaper 10 while the elastic members are in an unstretched condition. Still other means, such as heat-shrink elastic material, may be used to form the front and rear waist elastic members.

Leg elastic members 29 may comprise a carrier sheet (not shown) to which are attached a grouped set of elastics composed of a plurality of individual elastic strands. The elastic strands may intersect, or be interconnected, or be entirely separated from each other, The shown carrier sheet may, for example, comprise a 0.002 cm thick film of unembossed polypropylene material. The shown elastic strands can, for example, be composed of Lycra® elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, leg elastics 29 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 0.75–1.5 inches inward from the outer most edge of the set of elastic strands. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance within the range of about 0–8 cm toward either the front or rear portion of the diaper to provide desired fit and appearance. In particular embodiments of the invention, the innermost point (apex) of the set of curved elastics can be offset about 0–12 cm towards the front or rear portion of the diaper, and the outwardly bowed, reflexed-portion can be positioned toward the diaper front portion.

The absorbent material 16 is adapted to absorb body exudates. Any material capable of performing such a function is believed suitable for use in the present invention. The absorbent material may comprise a single, integral piece of material or, alternatively, may comprise a plurality of individual, separate pieces of material which are operably assembled together. The absorbent material 16 may be manufactured in a wide variety of sizes and shapes (for example, rectangular, trapezoidal, T-shaped, I-shaped, hourglass shaped, etc.), and from a wide variety of materials. The size and the absorbent capacity of the absorbent material 16 should be compatible with the size of the intended wearer and the liquid loading imparted by the intended use of the absorbent article. The size and the absorbent capacity of the absorbent material 16 can be varied to accommodate wearers ranging from infants through adults.

Various types of wettable hydrophilic fibrous material can be used to form the absorbent material 16. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of inherently wettable material, such as glass fibers; synthetic fibers made from inherently wettable thermoplastic polymers, such as particular polyester or polyamide fibers; and synthetic fibers composed of a non-wettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the non-wettable, hydrophobic fiber with a hydrophilic polymer during or after the formation of the fiber. For the purposes of the present invention, it is contemplated that selected blends of the various type of fibers mentioned above may also be employed. As used herein, the term "hydrophilic" describes fibers or the surfaces of fibers, which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 surface force analyzer system. When measured with this system, fibers having contact angles less than 90 degrees are designated "wettable", while fibers having contact angles greater than 90 degrees are designated "non-wettable".

In addition to the fibrous material described above, the absorbent material 16 may further comprise a high-absorbency material such as those known in the art as "superabsorbents". High-absorbency materials can be natural, synthetic, and modified natural polymers and materials. In addition, the high-absorbency materials can be inorganic materials such as silica gels, or organic compounds such as crosslinked polymers. The term "crosslinked" refers to any means for effectively rendering normal water-soluble materials substantially water insoluble but swellable. Such means can include, for example, physical entanglement, crystalline domains, covalent bonds, ionic complexes and associations, hydrophilic associations such as hydrogen bonding, and hydrophobic associations or van der Waals forces.

Examples of synthetic high-absorbency materials include polymeric materials, such as alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol) and mixtures and copolymers thereof. Further polymers suitable for use in the absorbent material include natural and modified natural polymers, such as hydrolyzed acrylonitrile-grafted starch, acrylic acid grafted starch, methyl cellulose, carboxymethyl cellulose, hydroxypropyl cellulose, carboxymethyl starch, and the natural gums, such as alginates, xanthan gum, locust bean gum, and the like. Mixtures of natural and wholly or partially synthetic absorbent polymer can also be useful in the present invention. Other suitable high-absorbency materials are disclosed by Assarson et al. in U.S. Pat. No. 3,902,236 issued Aug. 26, 1975. Processes for preparing synthetic: high-absorbency materials are disclosed in U.S. Pat. No. 4,076,663 issued Feb. 28, 1978, to Masuda et al. and U.S. Pat. No. 4,286,082 issued Aug. 25, 1981, to Tsubakimoto et al.

Diaper configurations suitable for use in the present invention may include additional features, such as containment flaps, and are explained in greater detail in the following U.S. patents and patent applications, the disclosures of which are incorporated herein to the extent consistent herewith: U.S. Pat. application Ser. No. 07/757,760 filed Sep. 11, 1991, in the name of Hanson et al.; U.S. Pat. No. 4,149,335 issued Sep. 22, 1992, to Kellenberger et al.; U.S. Pat. No. 4,798,603 issued Jan. 17, 1989, to Meyer et al.; U.S. Pat. No. 4,704,116 issued Nov. 3, 1987, to Enloe; U.S. Pat. No 5,147,343 issued Sep. 15, 1992, to Kellenberger; U.S. Patent application Ser. No. 07/997,800 filed Dec. 29, 1992, in the name of McCormack et al. and U.S. patent application Ser. No. 08/148,130 filed Nov. 5, 1993, in the name of Dilnik et al.

As can be appreciated from the above description of the component materials from which the diaper 10 is formed, the body of the absorbent article, such as diaper body 44, is generally not elastic. As used herein, "elastic", "elastomeric", and the like refer to the ability of a material or composite to be elongated by at least about 50 percent and upon relaxation to return to within at least 50 percent of its original length. Thus, while the ears 24 are elastic, the body of the absorbent article to which the ears are intended to be attached is suitably non-elastic. This, of course, does not prevent the body of the absorbent article from including elastic components such as leg and waist elastics.

The fastener 30 may comprise any means suitable for fastening the elastomeric ear to the front portion of the article to secure the article about the waist of a wearer. In the illustrated embodiment, the fastener 30 comprises the hook material of a hook-and-loop fastener. Other suitable fasteners include adhesives, adhesive tapes, cohesives, snaps, buttons, latches, hooks, and the like. In many instances, the fastener 30 will require the presence of a mating fastener or attachment surface, such as loop material 32, on the front portion of the absorbent article.

The elastomeric ears of the present invention can be formed from any type of an elastomeric material capable of performing as described herein. As a general rule, the elastomeric material will be stretchable in at least one direction. Preferably, the elastomeric material will be stretchable in two directions. When the elastomeric material is stretchable in a single direction, the stretch direction of the elastomeric material will be oriented so as to provide elastomeric forces which tend to pull the front and rear portions of the article towards one another such that the article is maintained about the waist of a wearer.

It is generally preferred that the elastomeric material from which the ears are formed be capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material may be an inherently elastomeric material, that is, one which is formed in an elastomeric state, or may be rendered elastomeric through processing subsequent formation. For example, the elastomeric material may be heat or pressure activated.

In particular embodiments of the invention, the elastomeric ears comprise an elastomeric material, such as a stretch-bonded-laminate (SBL) material, a neck-bonded-laminate (NBL) material, an elastomeric film, an elastomeric foam material, or the like. For example, suitable meltblown elastomeric fibrous webs for forming the elastomeric ears are described in U.S. Pat. No. 4,663,220 issued May 5, 1987, to T. Wisneski et al., the disclosure of which is hereby incorporated by reference. Examples of composite fabrics comprising at least one layer of nonwoven textile fabric secured to a fibrous elastic layer are described in European Patent application EP No. 0 110 010 (Publication Number EP 0 217 031) published on Apr. 8, 1987 with the inventors listed as J. Taylor et al., the disclosure of which is hereby incorporated by reference. Examples of NBL materials are described in U.S. Pat. No. 5,226,992 issued Jul. 13, 1993 to Mormon, the disclosure of which is hereby incorporated by reference.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A disposable absorbent article, said article defining a front portion, a rear portion, and a crotch portion connecting the front and rear portions; said article comprising:

an outer cover;

a liquid-pervious bodyside liner;

an absorbent material located between said cover and said bodyside liner;

a pair of elastomeric ears attached to said rear portion, said ears having a proximal edge, a distal edge, a first connecting edge, and a second connecting edge, said first and second connecting edges connecting said proximal and distal edges, said second connecting edge being non-parallel to said first connecting edge and said proximal edge being longer than said distal edge;

a fastener joined to said elastomeric ears for attaching said elastomeric ears to said front portion in an overlapping relationship; wherein, when in use, said second connecting edge defines at least a portion of a leg opening.

2. The disposable absorbent article according to claim 1 wherein said proximal edge and said first connecting edge are generally perpendicular.

3. The disposable absorbent article according to claim 1 wherein said second connecting edge is concavely arcuate.

4. The disposable absorbent article according to claim 3 wherein said second connecting edge is defined by the arc of a circle having a radius of from about 1 inch (2.54 centimeters) to about 6 inches (15.24 centimeters).

5. The disposable absorbent article according to claim 4 wherein said second connecting edge is defined by the arc of a circle having a radius of from about 1.5 inches (3.8 centimeters) to about 4 inches (10.2 centimeters).

6. The disposable absorbent article according to claim 5 wherein said second connecting edge is defined by the arc of a circle having a radius of from about 2 inches (5.1 centimeters) to about 3.5 inches (8.9 centimeters).

7. The disposable absorbent article according to claim 3 wherein said second connecting edge is defined by the arc of two or more circles having a radius of from about 1 inch (2.54 centimeters) to about 6 inches (15.24 centimeters).

8. The disposable absorbent article according to claim 4 wherein said second connecting edge has a length defined by an included angle alpha of from about 50 degrees to about 130 degrees.

9. The disposable absorbent article according to claim 8 wherein said second connecting edge has a length defined by an included angle alpha of from about 80 degrees to about 100 degrees.

10. The disposable absorbent article according to claim 1 wherein said proximal edge is linear.

11. The disposable absorbent article according to claim 10 wherein said distal edge is generally parallel to said proximal edge.

12. The disposable absorbent article according to claim 1 wherein said distal edge has a length of from about 0.25 inch (0.635 centimeter) to about 6 inches (15.24 centimeters).

13. The disposable absorbent article according to claim 1 wherein said proximal edge has a length of from about 2 inches (5.1 centimeters) to about 7 inches (17.8 centimeters).

14. The disposable absorbent article according to claim 1 wherein the ratio of the length of said distal edge to the length of said proximal edge is from about 1:28 to about 3:4.

15. An elastomeric ear adapted for use on a disposable absorbent article, said ear comprising;
    a body of elastomeric material, said material defining a proximal edge, a distal edge, a first connecting edge, and a second connecting edge, said first and second connecting edges connecting said proximal and distal edges, said second connecting edge being non-parallel to said first connecting edge, and said proximal edge being longer than said distal edge; and
    a fastener joined to said elastomeric ears for releasably attaching said elastomeric ear to a substrate.

16. The elastomeric ear according to claim 15 wherein said proximal edge and said first connecting edge are generally perpendicular.

17. The elastomeric ear according to claim 15 wherein said second connecting edge is concavely arcuate.

18. The elastomeric ear according to claim 17 wherein said second connecting edge is defined by the arc of a circle having a radius of from about 1 inch (2.54 centimeters) to about 6 inches (15.24 centimeters).

19. The elastomeric ear according to claim 18 wherein said second connecting edge is defined by the arc of a circle having a radius of from about 1.5 inches (3.8 centimeters) to about 4 inches (10.2 centimeters).

20. The elastomeric ear according to claim 19 wherein said second connecting edge is defined by the arc of a circle having a radius of from about 2 inches (5.1 centimeters) to about 3.5 inches (8.9 centimeters).

21. The elastomeric ear according to claim 17 wherein said second connecting edge is defined by the arc of two or more circles having a radius of from about 1 inch (2.54 centimeters) to about 6 inches (15.24 centimeters).

22. The elastomeric ear according to claim 18 wherein said second connecting edge has a length defined by an included angle alpha of from about 50 degrees to about 130 degrees.

23. The elastomeric ear according to claim 22 wherein said second connecting edge has a length defined by an included angle alpha of from about 80 degrees to about 100 degrees.

24. The elastomeric ear according to claim 15 wherein said proximal edge is linear.

25. The elastomeric ear according to claim 24 wherein said distal edge is generally parallel to said proximal edge.

26. The elastomeric ear according to claim 15 wherein said distal edge has a length of from about 0.25 inch (0.635 centimeter) to about 6 inches (15.24 centimeters).

27. The elastomeric ear according to claim 15 wherein said proximal edge has a length of from about 2 inches (5.1 centimeters) to about 7 inches (17.8 centimeters).

28. The elastomeric ear according to claim 15 wherein the ratio of the length of said distal edge to said proximal edge is from about 1:28 to about 3:4.

29. The elastomeric ear according to claim 15 wherein said ear further comprises a non-elastomeric extension member attached to said distal edge.

30. The disposable absorbent article according to claim 1 wherein said elastomeric ear further comprises a non-elastomeric extension member attached to said distal edge.

* * * * *

(12) EX PARTE REEXAMINATION CERTIFICATE (8581st)
United States Patent
Kuepper et al.

(10) Number: US 5,496,298 C1
(45) Certificate Issued: Oct. 4, 2011

(54) ELASTOMERIC EARS FOR DISPOSABLE ABSORBENT ARTICLE

(75) Inventors: Rebecca J. Kuepper, Appleton, WI (US); Christine A. Rasmussen, Medford, WI (US)

(73) Assignee: Kimberly-Clark Worldwide, Inc., Neenah, WI (US)

Reexamination Request:
No. 90/010,828, Feb. 25, 2010

Reexamination Certificate for:
Patent No.: 5,496,298
Issued: Mar. 5, 1996
Appl. No.: 08/174,565
Filed: Dec. 28, 1993

(51) Int. Cl.
*A61F 13/15* (2006.01)

(52) U.S. Cl. .............. 604/389; 604/385; 604/358; 604/385.03; 604/385.21; 604/385.29; 428/284; 428/913

(58) Field of Classification Search .............. None
See application file for complete search history.

(56) References Cited

U.S. PATENT DOCUMENTS

| | | |
|---|---|---|
| 3,860,003 A | 1/1975 | Buell |
| 3,882,871 A | 5/1975 | Taniguchi |
| 4,209,016 A | 6/1980 | Schaar |
| 4,857,067 A | 8/1989 | Wood et al. |
| 4,861,652 A | 8/1989 | Lippert et al. |
| 4,895,568 A * | 1/1990 | Enloe .............. 604/385.27 |
| 4,916,005 A | 4/1990 | Lippert et al. |
| 4,936,840 A | 6/1990 | Proxmire |
| 4,938,753 A | 7/1990 | Van Gompel et al. |
| 4,940,464 A | 7/1990 | Van Gompel et al. |
| 5,019,073 A | 5/1991 | Roessler et al. |
| 5,098,423 A | 3/1992 | Pieniak et al. |
| 5,151,092 A | 9/1992 | Buell et al. |
| 5,176,670 A | 1/1993 | Roessler et al. |
| 5,176,671 A * | 1/1993 | Roessler et al. .............. 604/391 |
| 5,196,000 A | 3/1993 | Clear et al. |
| 5,246,433 A | 9/1993 | Hasse et al. |
| 5,261,901 A | 11/1993 | Guay |
| 5,358,500 A | 10/1994 | Lavon et al. |
| 5,370,634 A | 12/1994 | Ando et al. |
| 5,383,872 A | 1/1995 | Roessler et al. |
| 5,464,401 A | 11/1995 | Hasse et al. |
| 5,489,282 A | 2/1996 | Zehner et al. |
| 5,674,216 A | 10/1997 | Buell et al. |

FOREIGN PATENT DOCUMENTS

| | | |
|---|---|---|
| EP | 0323040 A1 | 7/1989 |
| EP | 0374542 A2 | 6/1990 |
| EP | 0532035 | 3/1993 |
| EP | 0701426 B1 | 3/1996 |
| GB | 2244422 | 12/1991 |

(Continued)

OTHER PUBLICATIONS

Defendant's Brief in Support of Their Motion for a Summary Judgment that all of the asserted claims of Plaintiff's U.S. Patent No. 5,496,298 are Invalid, Civil Action No. 1:09–cv–1685 (WWC), dated Jan. 5, 2010, *Kimberly–Clark Worldwide, Inc.* v *First Quality Baby Products, LLC, et al.*, 36 pages.

(Continued)

*Primary Examiner* — Glenn K. Dawson

(57) ABSTRACT

Disclosed is an elastomeric ear suitable for use on a disposable absorbent article. The elastomeric ear is formed from an elastomeric material which defines a proximal edge, a distal edge, a first connecting edge and a second connecting edge. The first and second connecting edges connect the proximal and distal edges. The second connecting edge is non-parallel to the first connecting edge, and the proximal edge is longer than the distal edge. A fastener is joined to the elastomeric ear. Also described is a disposable absorbent article including such an elastomeric ear.

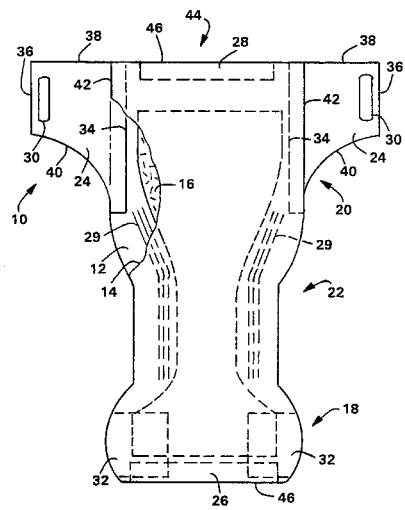

FOREIGN PATENT DOCUMENTS

| JP | 51-135753 | 11/1976 |
| --- | --- | --- |
| JP | H3-33623 | 4/1991 |
| JP | 03033623 | 4/1991 |
| JP | 03123550 | 5/1991 |
| JP | 4/4744 | 2/1992 |
| JP | 5-7219 | 2/1993 |
| WO | 9222274 A1 | 12/1992 |
| WO | 9324085 | 12/1993 |

OTHER PUBLICATIONS

Defendant's Statement of Material Facts in Support of Their Motion for Summary Judgement that all of the Asserted Claims of Plaintiff's U.S. Patent No. 5,496,298 are Invalid, Civil Action No. 1:09–cv–1685 (WWC), dated Jan. 5, 2010, *Kimberly–Clark Worldwide, Inc.* v *First Quality Baby Prodcuts, LLC, et al.*, 32 pages.

Kimberly–Clark Worldwide, Inc's Opposition to First Quality's Motion for Summary Judgment, Case No. 1:09–cv–01685–WWC, dated Mar. 8, 2010, *Kimberly–Clark Worldwide, Inc.* v *First Quality Baby Products, LLC, et al.*, 233 pages.

Defendants' Reply Brief In Support of Their Motion For A Summary Judgment That All of The Asserted Claims of Plaintiff's U.S. Patent No. 5,496,298 are Invalid, *Kimberly–Clark Worldwide, Inc.* v *First Quality Baby Products, LLC, et al.*, Civil Action No. 1:09–cv–1685 (WWC), dated Mar. 22, 2010, 114 pages.

Kimberly–Clark Worldwide, Inc.'s Sur–Reply in Opposition to First Quality's Motion for Summary Judgment, *Kimberly–Clark Worldwide, Inc.* v *First Quality Baby Products, LLC, et al.*, Case No. 1:09–cv–1685–WWC, dated Mar. 30, 2010, 6 pages.

Memorandum and Order Denying First Quality's Motion for Summary Judgment, *Kimberly–Clark Worldwide, Inc.* v *First Quality Baby Products, LLC, et al.*, Civil No. 1:CV–09–1685, dated Jul. 29, 2010, 17 pages.

Defendants' First Supplemental Responses to Plaintiff's First Set of Interrogatories (No. 4), *Kimberly–Clark Worldwide, Inc.* v *First Quality Baby Products, LLC, et al.*, Civil Action No. 1:09–cv–1685 (WWC), dated Nov. 12, 2009, 425 pages.

Plaintiff's Response to Defendants' Third Set of Interrogatories (No. 9), *Kimberly–Clark Worldwide, Inc.* v *First Quality Baby Products, LLC, et al.*, Case No. 1:09–cv–1685–WWC, dated Mar. 15, 2010, 29 pages.

Plaintiff's Responses to Defendants' Second Set of Interrogatories (Nos. 7–8), *Kimberly–Clark Worldwide, Inc.* v *First Quality Baby Products, LLC, et al.*, Case No. 1:09–cv–1685–WWC, dated Oct. 29, 2009, 359 pages.

Kimberly–Clark Worldwide, Inc.'s Memorandum in Support of Its Proposed Claim Constructions, *Kimberly–Clark Worldwide, Inc.* v *First Quality Baby Products, LLC, et al.*, Case No. 1:09–cv–1685–WWC, dated Mar. 4, 2010, 422 pages.

First Quality's Technical Tutorial, *Kimberly–Clark Worldwide, Inc.* v *First Quality Baby Products, LLC, et al.*, Case No. 1:09–cv–1685–WWC, dated May 27, 2010, 102 pages.

K–C's Technical Tutorial Presentation, *Kimberly–Clark Worldwide, Inc.* v *First Quality Baby Products, LLC, et al.*, Case No. 1:09–cv–1685–WWC, dated May 27, 2010, 73 pages.

First Quality's Claim Construction Demonstratives, *Kimberly–Clark Worldwide, Inc.* v *First Quality Baby Products, LLC, et al.*, Case No. 1:09–cv–1685–WWC, dated Jun. 9, 2010, 187 pages.

K–C's Markman Presentation (Kuepper, Ungpiyakul and Christoffel Patents), *Kimberly–Clark Worldwide, Inc.* v *First Quality Baby Products, LLC, et al.*, Case No. 1:09–cv–1685–WWC, dated Jun. 9, 2010, 85 pages.

Transcript of the Markman Hearing, *Kimberly–Clark Worldwide, Inc.* v *First Quality Baby Products, LLC, et al.*, Case No. 1:09–cv–1685–WWC, dated Jun. 9, 2010, 220 pages.

Amended Complaint, *Kimberly–Clark Worldwide, Inc.* v *First Quality Baby Products, LLC, et al.*, Case No. 1:09–cv–1685–WWC, dated Sep. 23, 2009, 317 pages.

Exhibit A—Second Amended Complaint, *Kimberly–Clark Worldwide, Inc.* v *First Quality Baby Products, LLC, et al.*, Case No. 1:09–cv–1685–WWC, dated Feb. 12, 2010, 22 pages.

Defendants' Answers, Affirmative Defenses, and Counterclaims to Plaintiff's Amended Complaint, *Kimberly–Clark Worldwide, Inc.* v *First Quality Baby Products, LLC, et al.*, Case No. 1:09–cv–1685–WWC, dated Oct. 2009, 45 pages.

Defendants' Answer to Second Amended Complaint and Counterclaims, *Kimberly–Clark Worldwide, Inc.* v *First Quality Baby Products, LLC, et al.*, Civil Action No. 1:09–cv–1685–WWC, dated Jul. 26, 2010, 99 pages.

Defendants' Fourth Supplemental Response to Plaintiff's First Set of Interrogatories (No. 3), *Kimberly–Clark Worldwide, Inc.* v *First Quality Baby Products, LLC, et al.*, Civil Action No. 1:09–cv–1685–WWC, dated Dec. 31, 2009, 23 pages.

First Quality's Responsive Claim Construction Brief, *Kimberly–Clark Worldwide, Inc.* v *First Quality Baby Products, LLC, et al.*, Case No. 1:09–cv–1685–WWC, dated Apr. 21, 2010, 594 pages.

Kimberly–Clark Worldwide, Inc.'s Reply Memorandum in Support of its Proposed Claim Constructions, *Kimberly–Clark Worldwide, Inc.* v *First Quality Baby Products, LLC, et al.*, Case No. 1:09–cv–1685–WWC, dated May 13, 2010, 75 pages.

Defendant Valor Brands, LLC's Answer, Affirmative Defenses, and Counterclaims to Kimberly–Clark Worldwide, Inc.'s Complaint, *Kimberly–Clark Worldwide, Inc.* v *Valor Brands, LLC and Grupo P.I. Mabe SA de CV a/k/a Mabesa*, Civil Action No. 3–08–CV–0872–G (BD), dated Jul. 25, 2008, 184 pages.

Kimberly–Clark Worldwide, Inc.'s Preliminary Infringement Contentions Pursuant to Miscellaneous Order No. 62, Kimberly–Clark Worldwide, Inc.'s Complaint, *Kimberly–Clark Worldwide, Inc.* v *Valor Brands, LLC and Grupo P.I. Mabe SA de CV a/k/a Mabesa*, Civil Action No. 08–0872–BD, dated Aug. 26, 2008, 15 pages.

Defendant Valor Brands, LLC's Answers and Objections to Plaintiff's First Set of Interrogatories, *Kimberly–Clark Worldwide, Inc.* v *Valor Brands, LLC and Grupo P.I. Mabe SA de CV a/k/a/ Mabesa*, Civil Action No. 3–08–0872–G (BD), dated Sep. 10, 2008, 27 pages.

Examination Decision of the Patent Reexamination Board for Chinese Patent Application No. 94195006.9, 14 pages.

Decision to Maintain the European Patent in Amended Form (Article 102(3) EPC) for European Application No. 95906732.3, 3 pages.

Communication Pursuant to Rule 58(5) EPC for European Application No. 95906732.3, 16 pages.

Decision dated Feb. 22, 2005 for European Application No. 95906732.3, 22 pages.
Minutes of the Oral Proceedings of Feb. 22, 2005 for European Application No. 95906732.3, 4 pages.
Letter to the European Patent Office dated Jan. 21, 2005 regarding the Summons to Oral Proceedings and the Preliminary Opinion, 12 pages.
Fax to the European Patent Office dated Jan. 21, 2005 from Elkington and Fife LLP, for European Application No. 95906732.3, 8 pages.
Letter to the European Patent Office dated Jan. 20, 2005 regarding Opposition against EP 0737057, 3 pages.
Summons to Oral Proceedings Pursuant to Rule 71(1) EPC for European Application No. 95906732.3, dated Jul. 14, 2004, 7 pages.
Letter to the European Patent Office enclosing further Submissions on behalf of the Patentee, dated Sep. 23, 2003, 24 pages.
Letter to the European Patent Office filing Grounds of Appeal for European Application No. 95906732.3, dated Feb. 28, 2003, 70 pages.
Letter to the European Patent Office regarding the Grounds of Appeal, dated Feb. 18, 2003, 5 pages.
Provision of a copy of the minutes in accordance with Rule 76(4) EPC for European Application No. 95906732.3, dated Oct. 24, 2002, 38 pages.
Observations under Rule 71a (EPC) on behalf of Opponent 03 for European Application No. 95906732.3, 11 pages.
Letter to the European Patent Office filing submissions under Rule 71a, dated Sep. 11, 2002, 37 pages.
Letter to the European Patent Office regarding Request for Revocation for EP0737057, dated Sep. 9, 2002, 2 pages.
Letter to the European Patent Office Responding to Opponent OIII's Letter of Jul. 17, 2002, dated Sep. 10, 2002, 14 pages.
Letter to the European Patent Office filing Observations on behalf of the Patentee, dated Oct. 17, 2001, 16 pages.
Letter to the European Patent Office regarding a further prior art document for European Application No. 95907632.3, dated Jul. 17, 2002, 15 pages.
Notice of Opposition by SCA Hygiene Products AB for EP 0737057 dated Dec. 18, 2000, 195 pages.
Notice of Opposition by The Procter & Gamble Company for EP 0737057 dated Mar. 22, 2000, 149 pages.
Notice of Opposition by Paul Hartmann AG for EP 0737057 dated Dec. 19, 2000, 110 pages.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-30 are cancelled.

New claims 31-34 are added and determined to be patentable.

*31. The disposable absorbent article according to claim 1 wherein the second connecting edge comprises a first segment and a second segment, the first segment extending outward from the proximal edge and being generally parallel to the first connecting edge, the second segment extending between the first segment and the distal edge and being non-parallel to said first connecting edge.*

*32. The disposable absorbent article according to claim 31 wherein the second segment of the second connecting edge is arcuate.*

*33. The disposable absorbent article according to claim 32 wherein the second segment of the second connecting edge is concavely arcuate.*

*34. A disposable absorbent article, said article defining a front portion, a rear portion, and a crotch portion connecting the front and rear portions; said article comprising:*

*an outer cover;*

*a liquid-pervious bodyside liner;*

*an absorbent material located between said cover and said bodyside liner;*

*a pair of elastomeric ears attached to said rear portion, said ears having a proximal edge, a distal edge, a first connecting edge, and a second connecting edge, said first and second connecting edges connecting said proximal and distal edges, said second connecting edge comprising a first segment and a second segment, at least the second segment of the second connecting edge being non-parallel to said first connecting edge and said proximal edge being longer than said distal edge;*

*a fastener joined to said elastomeric ears for attaching said elastomeric ears to said front portion in an overlapping relationship; wherein, when in use, said second connecting edge defines at least a portion of a leg opening;*

*wherein the first segment of the second connecting edge is generally parallel to the first connecting edge.*

\* \* \* \* \*

(12) EX PARTE REEXAMINATION CERTIFICATE (10303rd)
United States Patent
Kuepper et al.

(10) Number: US 5,496,298 C2
(45) Certificate Issued: Sep. 30, 2014

(54) ELASTOMERIC EARS FOR DISPOSABLE ABSORBENT ARTICLE

(75) Inventors: Rebecca J. Kuepper, Appleton, WI (US); Christine A. Rasmussen, Medford, WI (US)

(73) Assignee: Kimberly-Clark Worldwide, Inc., Neenah, WI (US)

Reexamination Request:
No. 90/012,940, Aug. 1, 2013

Reexamination Certificate for:
Patent No.: 5,496,298
Issued: Mar. 5, 1996
Appl. No.: 08/174,565
Filed: Dec. 28, 1993

Reexamination Certificate C1 5,496,298 issued Oct. 4, 2011

(51) Int. Cl.
*A61F 13/15* (2006.01)
*A61F 13/56* (2006.01)

(52) U.S. Cl.
USPC ...... 604/389; 604/385; 604/358; 604/385.03; 604/385.21; 604/385.29; 428/284; 428/913

(58) Field of Classification Search
None
See application file for complete search history.

(56) References Cited

To view the complete listing of prior art documents cited during the proceeding for Reexamination Control Number 90/012,940, please refer to the USPTO's public Patent Application Information Retrieval (PAIR) system under the Display References tab.

*Primary Examiner* — Jeffrey L. Gellner

(57) ABSTRACT

Disclosed is an elastomeric ear suitable for use on a disposable absorbent article. The elastomeric ear is formed from an elastomeric material which defines a proximal edge, a distal edge, a first connecting edge and a second connecting edge. The first and second connecting edges connect the proximal and distal edges. The second connecting edge is non-parallel to the first connecting edge, and the proximal edge is longer than the distal edge. A fastener is joined to the elastomeric ear. Also described is a disposable absorbent article including such an elastomeric ear.

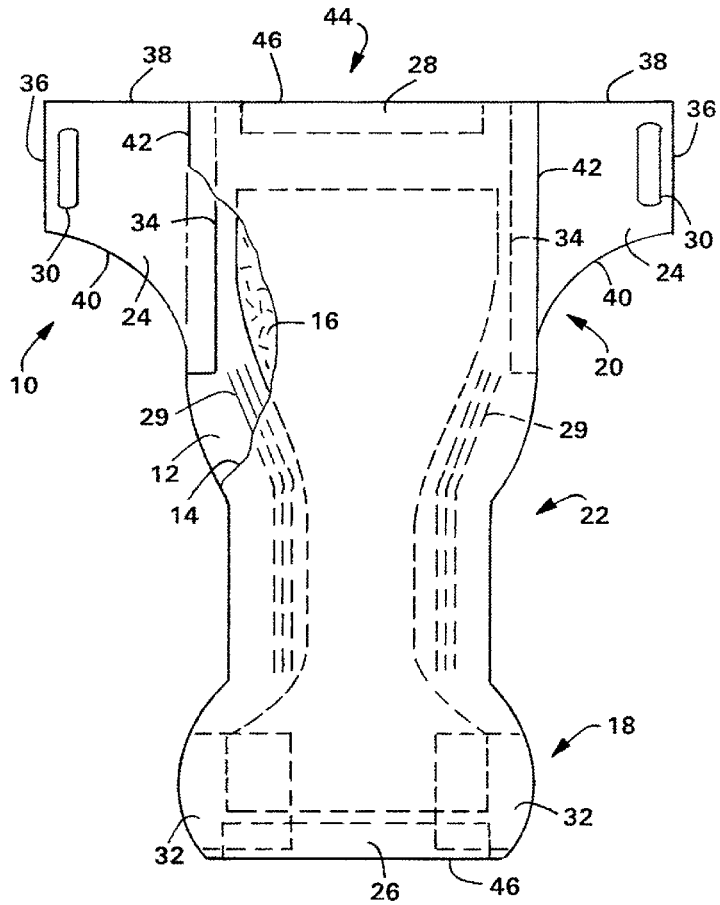

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 31-33 is confirmed.

Claims 1-30 were previously cancelled.

Claim 34 is cancelled.

\* \* \* \* \*